(12) United States Patent
Domke et al.

(10) Patent No.: US 9,792,750 B2
(45) Date of Patent: Oct. 17, 2017

(54) METHOD AND APPARATUS FOR CHECKING A VALUE DOCUMENT

(71) Applicant: GIESECKE & DEVRIENT GMBH, Munich (DE)

(72) Inventors: Jan Domke, Vaterstetten (DE); Ingo Scholz, Bremen (DE)

(73) Assignee: GIESECKE+DEVRIENT CURRENCY TECHNOLOGY GMBH, Munich (DE)

( * ) Notice: Subject to any disclaimer, the term of this patent is extended or adjusted under 35 U.S.C. 154(b) by 402 days.

(21) Appl. No.: 14/365,717

(22) PCT Filed: Dec. 19, 2012

(86) PCT No.: PCT/EP2012/005274
§ 371 (c)(1),
(2) Date: Jun. 16, 2014

(87) PCT Pub. No.: WO2013/091857
PCT Pub. Date: Jun. 27, 2013

(65) Prior Publication Data
US 2014/0338457 A1    Nov. 20, 2014

(30) Foreign Application Priority Data

Dec. 21, 2011   (DE) .................. 10 2011 121 913

(51) Int. Cl.
*G01N 29/07*   (2006.01)
*G01N 29/11*   (2006.01)
(Continued)

(52) U.S. Cl.
CPC ............... *G07D 7/08* (2013.01); *G01N 29/04* (2013.01); *G01N 29/4454* (2013.01); *G01N 29/07* (2013.01); *G01N 29/11* (2013.01)

(58) Field of Classification Search
CPC ............ G07D 7/08; G07D 7/06; G07D 7/004; G01N 29/04; G01N 29/07; G01N 29/12; G01N 29/11; G01N 29/4454; G01N 29/46

USPC ......... 73/597, 598, 599, 600, 645, 646, 648, 73/659
See application file for complete search history.

(56) References Cited

U.S. PATENT DOCUMENTS

| 6,763,721 B2 | 7/2004 | Wunderer et al. |
| 7,571,796 B2 | 8/2009 | Stenzel et al. |

(Continued)

FOREIGN PATENT DOCUMENTS

| DE | 103 35 147 A1 | 3/2005 |
| DE | 10 2004 036 229 A1 | 2/2006 |

(Continued)

OTHER PUBLICATIONS

International Preliminary Report on Patentability for International PCT Application No. PCT/EP2012/005274, Jun. 24, 2014.
(Continued)

*Primary Examiner* — Laura Martin
*Assistant Examiner* — Rose M Miller
(74) *Attorney, Agent, or Firm* — Workman Nydegger

(57) ABSTRACT

There is described a method for checking a value document of a specified type for the suspected presence of a forgery, in particular of a pieced-together forgery, wherein at least one ultrasonic property of the value document is captured in a spatially resolved manner so as to form location-dependent measuring data, wherein while employing the location-dependent measuring data it is checked whether there are present in a specified checking region of the value document two areal regions whose ultrasonic properties deviate from each other according to a specified difference criterion, and wherein there is formed an authenticity signal which represents the result of the check. Further, a corresponding checking device is described.

19 Claims, 6 Drawing Sheets

(51) Int. Cl.
    *G07D 7/08*           (2006.01)
    *G01N 29/44*        (2006.01)
    *G01N 29/04*        (2006.01)

(56)             References Cited

U.S. PATENT DOCUMENTS

| | | |
|---|---|---|
| 8,510,062 B2 | 8/2013 | Domke et al. |
| 2003/0025512 A1* | 2/2003 | Wunderer ............... G01N 29/11 324/639 |
| 2003/0183012 A1 | 10/2003 | Wunderer et al. |
| 2007/0187209 A1 | 8/2007 | Stenzel et al. |
| 2009/0074231 A1* | 3/2009 | Rancien ................. D21H 21/40 382/100 |
| 2009/0312957 A1 | 12/2009 | Domke et al. |
| 2010/0060881 A1 | 3/2010 | Kayani |
| 2010/0175842 A1 | 7/2010 | Patel et al. |
| 2010/0243729 A1 | 9/2010 | Russell et al. |
| 2010/0245043 A1 | 9/2010 | Doi et al. |

FOREIGN PATENT DOCUMENTS

| | | |
|---|---|---|
| DE | 10 2006 033 001 A1 | 1/2008 |
| WO | 0210716 A2 | 2/2002 |
| WO | 2008009384 A1 | 1/2008 |

OTHER PUBLICATIONS

International Search Report for corresponding International PCT Application No. PCT/EP2012/005274, mailed Apr. 3, 2013.

* cited by examiner

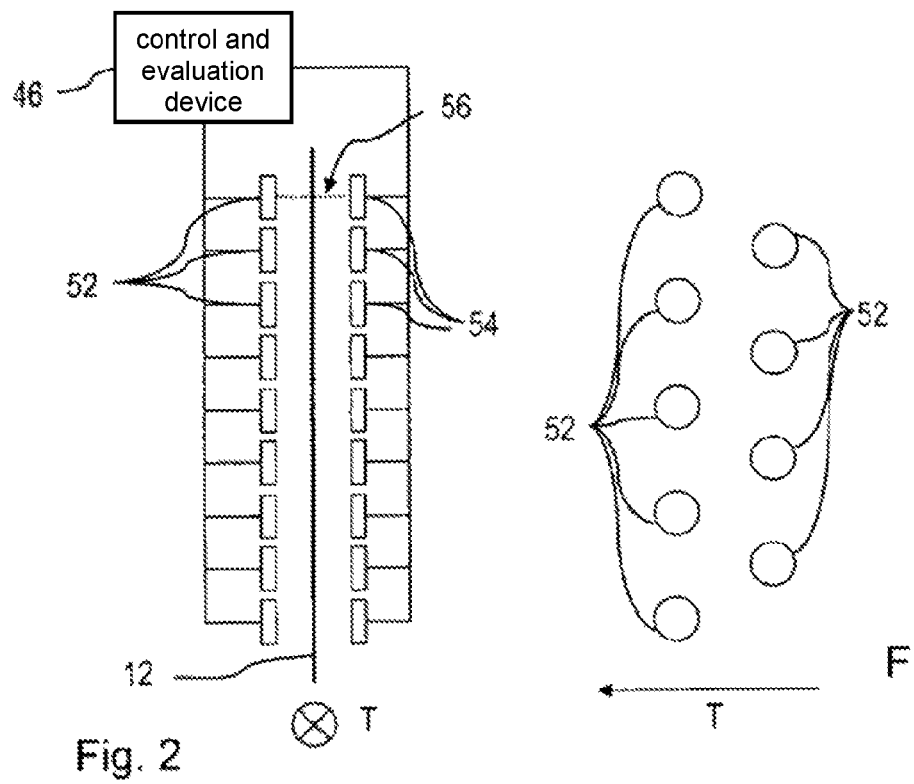
Fig. 2
Fig. 3
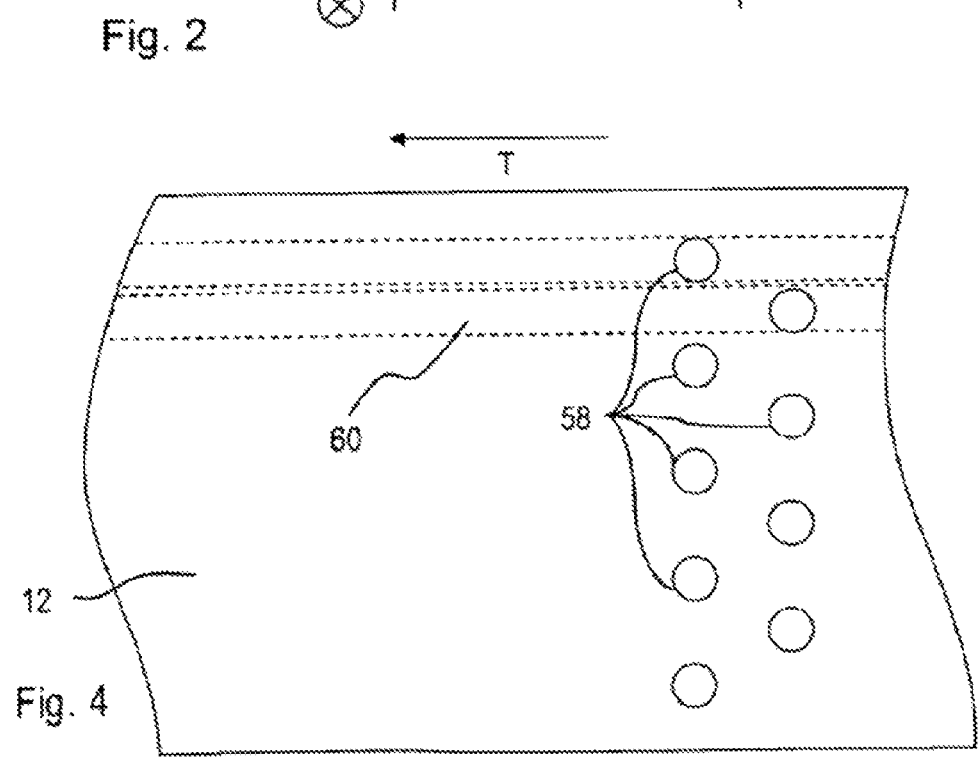
Fig. 4

METHOD AND APPARATUS FOR CHECKING A VALUE DOCUMENT

BACKGROUND

The present invention relates to a method for checking a value document of a specified type for the suspected presence of a forgery, in particular of a pieced-together forgery, and a device for carrying out the method.

Value documents are understood here to be sheet-shaped objects that represent for example a monetary value or an authorization and hence should not be manufacturable arbitrarily by unauthorized persons. They hence have features that are not simple to manufacture, in particular to copy, whose presence is an indication of authenticity, i.e. manufacture by an authorized body. Important examples of such value documents are chip cards, coupons, vouchers, checks and in particular bank notes. The value documents can respectively differ by their type, for example in the case of bank notes by the denomination or nominal value and the currency, or in the case of checks by a check-form type given by the issuer of the checks.

Forgeries of value documents occasionally appear that will hereinafter also be designated as pieced-together forgeries. They can be formed by connecting a detached part of a value document of a given type—usually by gluing—to a substrate portion, for example a detached part of a value document of a different type or a suitably shaped piece of paper, foil, etc., so as to produce an entity having approximately the dimensions of the value document. In particular, a value document can for example be skillfully divided into two parts which are then respectively joined together with a suitable substrate portion. This results in two forgeries of the value document which are difficult to recognize with simple checking apparatuses, depending on the execution of the forgery. A problem in the machine checking of such value documents is that the glued connection cannot be recognized easily and at the same time reliably.

SUMMARY

The present invention is hence based on the object of making available a method for checking a value document of a specified type for the suspected presence of a forgery, in particular of a pieced-together forgery, and providing a device for carrying out the method.

This object is achieved by a method for checking a value document of a specified type for the suspected presence of a forgery, in particular of a pieced-together forgery, wherein at least one ultrasonic property of the value document is captured by means of an ultrasonic sensor in a spatially resolved manner so as to form location-dependent measuring data, wherein by means of an evaluation device while employing the location-dependent measuring data it is checked, preferably by means of an evaluation device, whether two areal regions are present in a specified checking region of the value document, so that the at least one ultrasonic property has a specified first course at locations in a first one of the two areal regions, and the at least one ultrasonic property in the first areal region and the at least one ultrasonic property in the other areal region deviate from each other according to a specified difference criterion, and wherein there is formed an authenticity signal which represents the result of the check.

The object is further achieved by a device for checking value documents at least of a specified type which is configured for carrying out a method according to any of the preceding claims, and in particular preferably having an ultrasonic sensor which is configured for capturing in a spatially resolved manner at least one ultrasonic property of a value document transported through a capture region of the ultrasonic sensor so as to form location-dependent measuring data, and an evaluation device which is configured for capturing the measuring data of the ultrasonic sensor and checking while employing the location-dependent measuring data whether two areal regions are present in a specified checking region of the value document, so that the at least one ultrasonic property has a specified first course at locations in a first one of the two areal regions, and the at least one ultrasonic property in the first areal region and the at least one ultrasonic property in the other areal region deviate from each other according to a specified difference criterion, and forming an authenticity signal which represents the result of the check. The authenticity signal can be emitted or be employed further in the evaluation device, for example for storing a corresponding data value.

According to the invention, the value document is examined with ultrasound. For capturing the ultrasonic properties, ultrasound can be emitted onto the value document continuously or preferably in pulses, and the ultrasound thereupon emanating from the value document captured.

Ultrasound is understood within the framework of the present invention to be sound having a frequency greater than 20 kHz, preferably greater than 40 kHz. Particularly preferably, the frequency of the ultrasound lies under 800 kHz. When ultrasonic pulses are employed, the frequency is understood here to be the arithmetic average over the frequencies of the pulse.

The ultrasonic properties are established in a spatially resolved manner, i.e. the ultrasonic properties are established for different measuring regions of the value document, with at least some of the measuring regions possibly touching or overlapping each other. For each of the measuring regions, and thus a location on the value document that represents the respective measuring region, there can be formed a measurement value rendering the ultrasonic properties, which is processed further. The measuring data formed upon the measurement comprise the measurement values for the locations for which the measurement values were captured, and preferably respectively associated location information, which can, however, also result from the arrangement of the measurement values in a field.

According to the invention, it is checked whether two areal regions having different ultrasonic properties are present in a specified checking region of the value document. An areal region of the value document is understood within the framework of the present invention to be a contiguous region of the value document.

The checking region of the value document is specified in dependence on the specified type of the value document and can, depending on the type, comprise the total value document or also only a part of the same.

It is now checked whether the two areal regions are present.

The first one of the two areal regions is characterized in that the at least one ultrasonic property has a specified first course at locations in the areal region. The course of the ultrasonic property is understood within the framework of the present invention to be the variation of the ultrasonic property in the areal region or the absence thereof. The first course can preferably be specified in dependence on the type of the value document and, where applicable, the position upon the capture of the ultrasonic property. Since the measuring data represent the ultrasonic property, there corresponds to the course of the ultrasonic property a course of the measuring data that is accordingly understood to be the variation of the measuring data over the areal region or the absence of the variation. That the ultrasonic property has the specified first course at the locations in the first areal region is understood to mean that the measurement values given by the measuring data, or the measured course given thereby, correspond to the specified first course apart from fluctuations within a specified tolerance range. The size of the tolerance range can be chosen in particular in dependence on the properties of the ultrasonic sensor employed for the capture, and the manufacturing-based fluctuations of the properties of the value documents that determine the ultrasonic property. The first areal region can be given in particular by a portion of the value document onto or into which a piece of another document or sheet has been placed.

The other areal region results from it lying within the checking region and the at least one ultrasonic property in the first areal region and the at least one ultrasonic property in the other areal region deviating from each other according to a specified difference criterion. The difference criterion can be specified in dependence on the nature of the ultrasonic property and/or the type of the value document and/or the specified first course.

If the difference criterion is satisfied, this is regarded as an indication of a pieced-together forgery, and the evaluation device forms a corresponding authenticity signal. The authenticity signal can be emitted or be employed for storage of a data value in the evaluation device for later employment in an authenticity check.

The invention is characterized in particular in that it is unnecessary to recognize the connection of the parts of the composite value document, for example a glued connection. Use is instead made of the fact that the different parts differ by their ultrasonic properties.

The device according to the invention can be configured in particular for carrying out the method according to the invention. The evaluation device can in particular, for carrying out the check, contain a processor, for example a microcontroller or a digital signal processor, and/or an FPGA as well as a memory. The memory can store in particular instructions of a computer program, upon whose execution by the processor, method steps of the method according to the invention are performed after the capture of the measuring data.

As an ultrasonic property there can in principle be employed any suitable property that characterizes the interaction of the value document with ultrasound. Preferably, there can be employed ultrasound in a specified frequency range, particularly preferably in the range between 40 kHz and 800 kHz, very particularly preferably in the range between 100 kHz and 450 kHz, for which purpose the ultrasonic transducers serving as transmitters and receivers can be configured accordingly.

According to a preferred embodiment, there can be employed as an ultrasonic property the transmission or transmissivity to ultrasound in the specified frequency range. Then, for establishing the at least one ultrasonic property, ultrasound can be emitted onto the value document and the ultrasound transmitted by the value document captured. For this purpose, in the device, the ultrasonic sensor can be configured for emitting ultrasound onto the value document and capturing ultrasound transmitted by the value document. As transmission there can be employed the intensity of the transmitted ultrasound, or the intensity of the transmitted ultrasound normalized with the intensity of the ultrasound falling on the value document, or a value proportional thereto. It has turned out that ultrasound transmission properties are especially well suited for examining value documents, since they allow robust measurements.

According to another embodiment, however, it is alternatively or additionally possible to employ as an ultrasonic property the remission or remissivity to ultrasound in the specified frequency range. In the method, for establishing the at least one ultrasonic property in the specified frequency range, ultrasound can then be emitted onto the value document and the ultrasound remitted by the value document captured. In the device, the ultrasonic sensor can for this purpose preferably be configured for emitting ultrasound in the specified frequency range onto the value document and capturing ultrasound remitted by the value document. As remission there can be employed the intensity of the remitted ultrasound, or the intensity of the remitted ultrasound normalized with the intensity of the ultrasound falling on the value document, or a value proportional thereto.

It is for example also possible, however, to capture a phase change upon remission or transmission as an ultrasonic property.

Establishing the areal regions can be effected in principle arbitrarily. The manner of establishment can be chosen in particular in dependence on the specified first course. Thus, for establishing the areal regions there can first be established contiguous line regions in the transport direction or transverse to the transport direction, i.e. directly neighboring locations on a straight line in the transport direction or transverse to the transport direction, along which the ultrasonic properties have a course corresponding to the specified first course. Thereafter the areal regions can then be searched for on this basis. However, it is also possible that the measurement values corresponding to the locations are regarded as a field, and contiguous regions are searched for in this field. This method is particularly preferable when the specified course constitutes a pattern that provides a systematic local variation of the ultrasonic property.

According to a preferred embodiment, when checking whether the two areal regions are present in the specified checking region of the value document, averages over the measuring data over at least three neighboring locations can be formed and employed for establishing the course in the first areal region and/or when checking the distinguishing criterion. In the device, the evaluation device can for this purpose preferably be further so configured that, when checking whether the two areal regions are present in the specified checking region of the value document, averages over the measuring data over at least three neighboring locations are formed and employed for establishing the course in the first areal region and/or when checking the distinguishing criterion. This embodiment has the advantage that fluctuations due to use in the at least one ultrasonic property of the value document, or noise influences of the ultrasonic sensor employed for capturing the ultrasonic property, cannot have any, or any great, adverse effect on the check. In particular, for each of the measurement values for a respective location in the checking region, the respective measurement value can be replaced by the average over the measurement value for the respective location and at least two neighboring locations.

The first course can be specified in dependence on the type of the value document and preferably also on the checking region. For example, the first specified course can be such that in the first areal region according to a specified criterion the at least one ultrasonic property is location-independent, or that the measurement values are location-independent. They then show a location-independent course.

In the device, the evaluation device can for this purpose be so configured that the first specified course is such that in the first areal region according to a specified criterion the at least one ultrasonic property is location-independent, or that the measurement values are location-independent. This can be the case for example in value documents in the form of bank notes when the checking region has no watermark, but only has a simple bank-note substrate without any further elements. In this case, the check for the presence of the areal regions is especially easy to carry out. The criterion can be so chosen for example that random fluctuations in the measuring data or in the properties of the value document play only a very small, or no, part. Thus, the first course can be for example so defined that the variation of the measuring data, or the measurement values around the average thereof or around a value specified for the value-document type, must lie within a specified interval. The width of the interval can be chosen, inter alia, in dependence on the stated random influences. Further, the interval can be chosen in dependence on the type of the value document and preferably also the employed ultrasonic sensor. When the measuring data are preprocessed and/or averaged and/or filtered before the evaluation, this fact is preferably taken into consideration when fixing the interval.

It is for example also possible, however, that the first specified course constitutes a local pattern of the at least one ultrasonic property, said pattern being specified for the type of the value document. In the device, the evaluation device can for this purpose be so configured that the first specified course constitutes a local pattern of the at least one ultrasonic property, said pattern being specified for the type of the value document. This pattern may preferably be a watermark extending over the total checking region and preferably being periodic.

The difference criterion can relate to different properties of the value document, but is preferably chosen in dependence on the specified first course. Each one of the hereinafter stated subcriteria can be employed as the only subcriterion of the distinguishing criterion, but it is also possible in other embodiments that the distinguishing criterion comprises the subcriteria as alternatives or cumulatively.

Thus, in a preferred variant wherein the first specified course is such that in the first areal region according to a specified criterion the at least one ultrasonic property is location-independent, or that the measurement values representing the at least one ultrasonic property in the measuring data are location-independent, the difference criterion can contain the subcriterion of whether the areal regions' weights per unit area corresponding to the measuring data, or weights per unit area of the areal regions represented by the measuring data, differ by at least 5 $g/m^2$, preferably 10 $g/m^2$. In the device, the evaluation device can for this purpose preferably be so configured that the first specified course is such that in the first areal region according to a specified criterion the at least one ultrasonic property is location-independent, or that measurement values in the measuring data representing the at least one ultrasonic property are location-independent, and that the difference criterion contains the subcriterion of whether the areal regions' weights per unit area corresponding to the measuring data, or weights per unit area of the areal regions fixed by the measuring data, differ by at least 5 $g/m^2$, preferably 10 $g/m^2$. The phrase "weights per unit area of the areal regions" is understood here to mean, on the one hand, different weight per unit area values or corresponding measurement values or values established therefrom that correspond to locations in the respective areal regions. On the other hand, the phrase is also understood to mean values established from the measuring data that represent the weight per unit area of the respective areal regions. The employment of this subcriterion makes it possible to recognize in particular pieced-together forgeries in which parts of the value document are replaced by more readily available paper portions, for example made of commercially available copying or printing paper. Further, it is possible to recognize pieced-together forgeries in value-document systems having different value-document types made of carrier materials, for example paper or plastic foils, with different weights per unit area respectively specified for the value-document type. It is then no longer possible to employ parts of a value document of lower value for replacing parts of a value document of higher value. The subject matter of the invention is hence also a system of value documents which comprises at least two different value-document types which respectively have a carrier material specific to the respective value-document type, preferably bank-note paper and/or plastic-foil substrates for bank notes and/or composite materials made of paper and foils, with a weight per unit area specific to the respective value-document type, with the weights per unit area differing for at least different value-document types. Preferably, the difference of the weights per unit area amounts to at least 5 $g/m^2$, particularly preferably at least 10 $g/m^2$. The carrier material can have window regions or feature regions in or on which foils or security features or watermarks or the like are located; these regions are not taken into consideration when establishing the weight per unit area, i.e. the checking region is so chosen that these features do not lie in the checking region.

According to another preferred variant wherein the first specified course represents a local pattern of the at least one ultrasonic property, said pattern being specified for the type of the value document, the difference criterion can contain the subcriterion of whether the measuring data for the other one of the areal regions represent a deviating, or no, local pattern of the at least one ultrasonic property. In the device, the evaluation device can for this purpose preferably be so configured that the difference criterion contains the subcriterion of whether the measuring data for one of the areal regions represent a local pattern of the at least one ultrasonic property, said pattern being specified for the type of value document, and whether the measuring data for the other one of the areal regions represent a deviating, or no, local pattern of the at least one ultrasonic property. Preferably, there can be employed as a pattern a watermark configured over the total value document. That one pattern deviates from the other pattern is also understood to mean that a deviation is present when the two patterns are displaced relative to each other in a manner that is impermissible for the value-document type, as can occur for example with a periodically configured watermark extending in a strip shape over the total value document.

To increase the recognition reliability, in the method, the check can preferably further involve checking whether the areal regions are separated by a continuous curve or line from a first edge portion of the value document to a second edge portion of the value document, i.e. lie on mutually opposing sides of the curve or line. In the device, the evaluation device can for this purpose be configured accordingly. The presence of such areal regions is an especially strong indication of the presence of a pieced-together forgery. The difference criterion can be chosen in principle arbitrarily, but suitably. It can preferably be chosen in dependence on the properties of the ultrasonic sensor employed for the examination and on the type of the value document to be examined.

Further, it is preferred that when checking whether the two areal regions are present, only those areal regions are taken into consideration whose surface areas exceed a specified minimum surface area. This minimum surface area can preferably be specified in dependence on the specified type of the value document, particularly preferably the security features of the value document. In the device, the evaluation device can for this purpose further be so configured that when checking whether the two areal regions are present, only those areal regions are taken into consideration whose surface areas exceed a specified minimum surface area. The minimum surface area can be specified for example in dependence on the size of security features or value-document portions on an authentic value document of the specified type that are typically replaced in a pieced-together forgery.

Alternatively or additionally, in the method, it is possible that the value document has a circumferential edge, and that, in the method, when checking whether the two areal regions are present, only those areal regions are taken into consideration that are limited by portions of the edge that do not extend colinearly. For this purpose, in the device, the evaluation device can be so configured that when checking whether the two areal regions are present, only those areal regions are taken into consideration that are limited by portions of a circumferential edge of the value document that do not extend colinearly. Collinear portions of the edge are understood here to be portions lying on a straight line. Mutually opposing portions of the edge, or portions of the edge that adjoin each other at a corner, of a rectangular value document are not collinear, for example.

Further, in the method, it can preferably be provided that the method is designed for checking value documents of at least two different specified value-document types, and a value-document type of the value document is established, and the checking region is fixed in dependence on the established value-document type. In the device, the evaluation device can for this purpose be so configured that the checking region is fixed in dependence on an established type of the value document. For establishing the type of the value document, there can in particular also be employed data of at least one other physical property of the value document, for example optical properties or the dimensions of the value document, which can be captured with suitable sensors, for example at least one optical sensor.

Further subject matter of the invention is a method for processing value documents while employing a value-document processing device which has a transport path having at least two transport branches, wherein a value document is checked with a checking method according to any of the previous claims and fed to one of the transport branches in dependence on the authenticity signal formed upon the check. Further subject matter of the invention is an apparatus for processing value documents, preferably sorting value documents, having a feeding device for value documents to be processed, an output device for value documents which has at least two output portions for receiving processed value documents, a transport device for transporting singled value documents from the feeding device along a transport path to the output device, a checking device according to the invention which is so disposed that the transport path extends through its capture region, and a control device which so actuates the transport device in dependence on an authenticity signal of the checking apparatus for a value document transported by the transport device that the value document is transported into an output portion of the two output portions that corresponds to the authenticity signal. In particular, according to a preferred variant, the value document can be fed to an output portion for value documents regarded as authentic only when the authenticity signal is absent or represents no indication of a forgery.

In the apparatus, it is preferred that said apparatus has a sensor which is so disposed that it can capture properties of a value document transported by means of the transport device, said properties being determined by the sensor, and can form measuring data representing them, and an establishing device which establishes a type of the value document in dependence on the measuring data and forms a type signal representing the type. Then the evaluation device of the checking device can be so configured that upon the check it does not take into consideration measuring data of the ultrasonic sensor in dependence on the type signal of the establishing device for regions outside the value document's checking region specified in dependence on the type of the value document.

BRIEF DESCRIPTION OF THE DRAWINGS

The invention will hereinafter be explained further by way of example with reference to the drawings. There are shown:

FIG. 2a schematic representation of an ultrasonic sensor of the bank-note processing apparatus in FIG. 1 having a control and evaluation device in a view along a transport direction of bank notes, FIG. 3a schematic representation of ultrasonic transmitters of the ultrasonic sensor in FIG. 2 in a plane parallel to the plane of a bank note to be examined, FIG. 4a schematic partial representation of a bank note having spots or sensing regions acoustically irradiated by the ultrasonic transmitters of the ultrasonic sensor in FIG. 2, FIG. 5a schematic representation of a bank note having locations or sensing regions for which transmission values have been established by means of the ultrasonic sensor in FIG. 3, FIG. 6 schematic representations of an authentic bank note (a) and of pieced-together forgeries (b-d), FIG. 7 schematic representations of an authentic bank note (a) having a large-area periodic watermark, and of pieced-together forgeries (b and c), FIG. 8a simplified flowchart for an example of a method for checking a value document of a specified type for the suspected presence of a forgery, in particular of a pieced-together forgery, and FIG. 9a simplified flowchart for a further example of a method for checking a value document of a specified type for the suspected presence of a forgery, in particular of a pieced-together forgery.

DETAILED DESCRIPTION OF VARIOUS EMBODIMENTS

Figure 1:
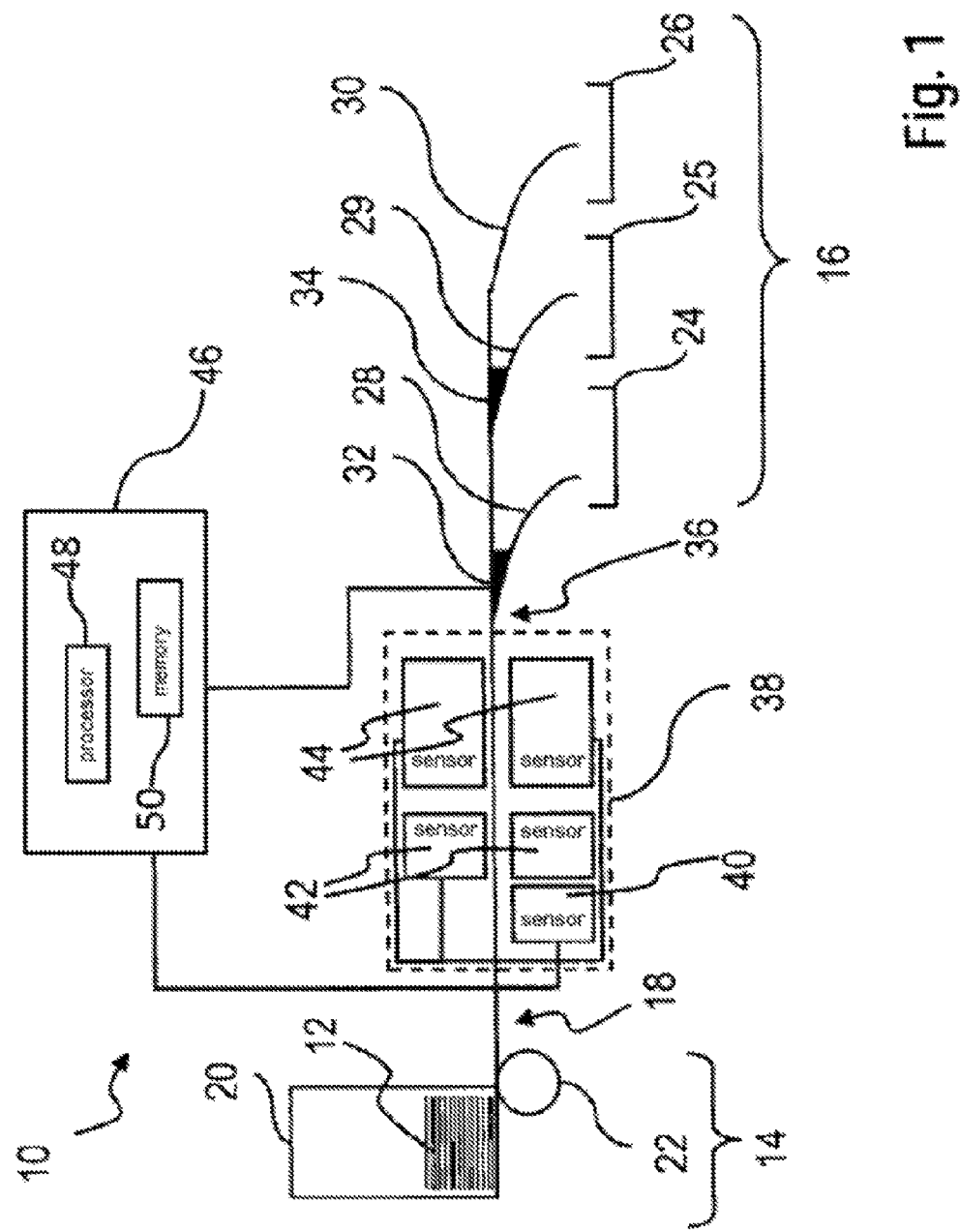
FIG. 1a schematic representation of a bank-note processing apparatus.

A value-document processing apparatus 10 in FIG. 1, in the example an apparatus for processing value documents 12 in the form of bank notes, is configured for sorting value documents in dependence on the recognition of the authenticity of processed value documents.

It has a feeding device 14 for feeding value documents, an output device 16 for receiving processed, i.e. sorted, value documents, and a transport device 18 for transporting singled value documents from the feeding device 14 to the output device 16.

The feeding device 14 comprises, in the example, an input pocket 20 for a value-document stack, and a singler 22 for singling value documents out of the value-document stack in the input pocket 20.

The output device 16 comprises, in the example, three output portions 24, 25 and 26 into which processed value documents can be sorted according to the result of the processing. In the example, each of the portions comprises a stack pocket and a stacking wheel (not shown) by means of which fed value documents can be deposited in the stack pocket.

The transport device 18 has at least two, in the example three, branches 28, 29 and 30 at whose ends one of the output portions 24, 25, 26 is respectively disposed, and, at the branching points, gates 32 and 34 controllable by actuating signals by means of which value documents can be fed to the branches 28 to 30 and thus to the output portions 24 to 26 in dependence on actuating signals.

On a transport path 36 defined by the transport device 18 between the feeding device 14, in the example more precisely the singler 22, and the first gate 32 after the singler 22 in the transport direction there is disposed a sensor device 38 which measures physical properties of the value documents when value documents are being transported past, and forms sensor signals representing the measurement results. In this example, the sensor device 38 has three sensors, namely an optical remission sensor 40 which captures a remission color image of the value document, an optical transmission sensor 42 which captures a transmission image of the value document, and a transmission ultrasonic sensor 44 which captures or measures ultrasound transmission properties of the value document in a spatially resolved manner.

A control and evaluation device 46 is connected via signal connections to the sensor device 38 and the transport device 18, in particular the gates 32 and 34. In connection with the sensor device 38, it classifies for a value document in dependence on the sensor signals of the sensor device 38 in one of specified authenticity classes and, by emitting actuating signals, so actuates the transport device 18, here more precisely the gates 32, 34, that the value document is output, in accordance with its class established upon the classification, to an output portion of the output device 16 that is associated with the class. The association with one of the specified authenticity classes, or the classification, is effected here in dependence on at least one specified authenticity criterion.

The control and evaluation device 46 has for this purpose in particular, besides corresponding interfaces for the sensor device 38 or its sensors, a processor 48 and a memory 50 which is connected to the processor 48 and stores at least one computer program with program code upon whose execution the processor 48 controls the apparatus or evaluates the sensor signals, in particular for establishing an authenticity class of a processed value document, and actuates the transport device 18 in accordance with the evaluation.

More precisely, while the value document is being transported past, the sensors capture, in accordance with their function, sensing-region properties of sensing regions on the bank note that are determined by the position of the sensors relative to the bank note, whereby the corresponding sensor signals are formed. Each of the sensors can have a different spatial resolution, i.e. the size and distribution of the captured sensing regions on the bank note can vary in dependence on the respective sensor and the transport speed employed. Each of the sensing regions has associated therewith a location that represents the position of the sensing regions for the respective sensor relative to each other and/or relative to the bank note.

The control and evaluation device 46 then establishes from the analog or digital sensor signals of the sensors of the sensor device 38 upon a sensor-signal evaluation at least one sensing-region property and/or at least one value-document property that is relevant for testing the bank notes with respect to their authenticity. Preferably, a plurality of these properties are established. In this example, there are established as optical sensing properties a transmission image and a remission image, and as an acoustic property the ultrasound transmission of the sensing regions.

In dependence on the sensing-region properties, the control and evaluation device 46 establishes for the different sensors respective authenticity signals that represent whether or not the established sensing-region or value-document properties represent an indication of the authenticity of the value document. In consequence of these signals, corresponding data can be stored in the control and evaluation device 46, for example the memory 50, for later employment. In dependence on the authenticity signals, the control and evaluation device 46 then establishes an overall result for the authenticity check according to a specified overall criterion, and forms the control signal for the transport device 18 in dependence on the result.

For processing value documents 12, value documents 12 inserted into the input pocket 20 as a stack or singly are singled by the singler 22 and fed in singled form to the transport device 18, which transports the singled value documents 12 past the sensor device 38. The latter captures the properties of the value documents 12, whereby sensor signals are formed which represent the properties of the respective value document. The control and evaluation device 46 captures the sensor signals, establishes in dependence thereon an authenticity class of the respective value document, and so actuates the gates in dependence on the result that the value documents are transported in accordance with the established authenticity class into an output portion associated with the respective authenticity class.

For establishing an authenticity class on the basis of ultrasonic properties there is used the transmission ultrasonic sensor 44, which, in the example, is constructed as follows (cf. FIGS. 2 and 3).

The sensor 44 has a plurality of ultrasonic transducers 52 disposed both transversely to a transport direction T of the value documents 12 and longitudinally thereto substantially in a plane parallel to a direction along the transport path 36 of the transported value document 12, and actuated by the control and evaluation device 46, for emitting ultrasonic pulses onto the bank note. These ultrasonic transducers 52 thus serve as ultrasonic transmitters.

Disposed opposite the ultrasonic transducers or transmitters 52 relative to the transport path 36 are the same number of ultrasonic transducers 54 serving as ultrasonic receivers, which so disposed to the control and evaluation device 46 via interfaces not shown in the figures and schematically shown signal connections that they can receive ultrasonic waves that emanate from a value document 12 transported along the transport path 36 and are caused by acoustic irradiation with ultrasonic pulses of the ultrasonic transmitters 52.

Each of the ultrasonic transmitters 52 has associated therewith one of the ultrasonic receivers 54 such that there results therebetween an ultrasonic path 56 extending at least approximately orthogonally to a value document 12 transported along the transport path 36, along which ultrasonic path an ultrasonic pulse emitted by the respective ultrasonic transmitter 52 runs to the ultrasonic receiver 54 associated therewith. With each pair of ultrasonic transmitters and ultrasonic receivers associated therewith or with each ultrasonic path 56 in connection with the control and evaluation device 46, it is thus possible to establish a value for the ultrasound transmission of the value document 12 at the location acoustically irradiated with the ultrasound.

The ultrasonic transducers 52, 54 are so configured that they are well suited for emitting or receiving ultrasonic pulses with a duration in the range of about 30 μs, in the example, and an ultrasonic frequency, i.e. a frequency maximum of the spectrum of the ultrasonic pulse, of about 400 kHz, in the example. Further, they are so dimensioned that a respective spot 58, i.e. sensing region, acoustically irradiated upon acoustic irradiation with the ultrasonic pulses on a value document 12 transported along the transport path 36 has a diameter of about 2 mm. Each of the sensing regions has associated therewith, as the location, the center of the sensing region.

The ultrasonic transmitters 52 and ultrasonic receivers 54 are so disposed in a plane parallel to the value document 12 in the transport path 36 that values for the ultrasound transmission are capturable for strip-shaped capture regions 60 extending parallel to the transport direction T, as represented in FIG. 4 for an instantaneous view during capture.

Figure 5:
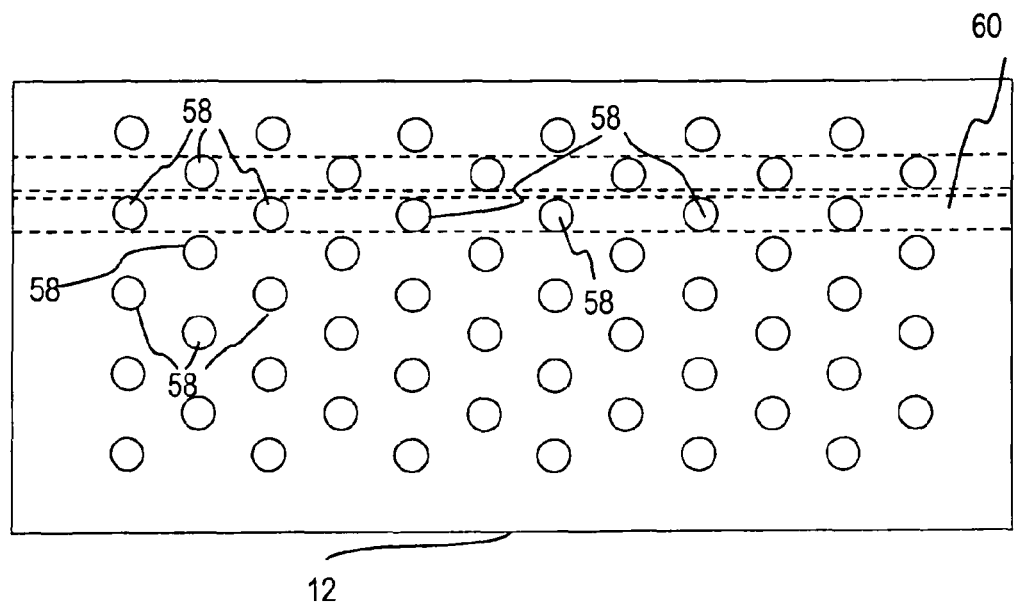

Altogether, there can thus result a distribution, represented for a value document 12 schematically in FIG. 4 and in particular FIG. 5, of sensing regions 58 or locations for which transmission values are capturable when the value document 12 is transported through the ultrasonic paths 56 at a constant, suitably specified speed and transmission values are captured at specified time intervals during said transport. In this exemplary embodiment, the actuation is effected independently of the entry of a value document 12 into the capture region of the transmission ultrasonic sensor 44. To suppress an unwanted reception of ultrasonic pulse echoes, the respective ultrasonic receiver for an ultrasonic path can be switched on at a delay of somewhat less than the pulse transit time for the ultrasonic path, relative to the time when the ultrasonic pulse is emitted by the ultrasonic transmitter for the ultrasonic path, and be switched off again before twice the pulse transit time since emission.

There thus results a regular arrangement of the sensing regions 58 or locations on the value document 12, in the example a substantially hexagonal arrangement. The arrangement of the ultrasonic transmitters 52 and ultrasonic receivers 54 is so chosen that the distance between consecutive locations in at least one of the strips or capture regions 60 is smaller than 1 cm, preferably smaller than 5 mm. In the example, the distance of nearest neighboring locations amounts to about 3 mm, preferably 2 mm.

The sensor 44 has, in the exemplary embodiment, in particular twenty-four ultrasonic transmitter/receiver pairs or ultrasonic paths 56, which are so disposed that the capture regions 60 or the tracks have a distance between 3 and 4 mm.

For capturing the transmission values, i.e. the transmission, the control and evaluation device 46 captures at constant time intervals the sensor signals of the ultrasonic receivers 54 which represent the intensity or power of individual receiving ultrasonic pulses as a function of time and thus, due to the constant transport speed, also of location. Using these signals, the control and evaluation device 46 also establishes the entry of a value document into the capture region of the sensor 44. The transmission values are given here simply by the received ultrasonic pulse energies, assuming a basically constant transmit power of the ultrasonic transmitters 52. In other exemplary embodiments, however, it is also possible to divide the received ultrasonic pulse energies by a specified or measured ultrasonic pulse energy of transmitted pulses and thus obtain normalized transmission values.

The established transmission values are stored so as to be associated with the locations for which they were captured. This can be effected for example in such a way that the transmission values are stored in the memory 50 in the time sequence of their capture separately for each of the capture regions 60. The capture region 60 then corresponds to a coordinate in a direction transverse to the transport direction, and the position in the row along the capture region 60 to a coordinate in the transport direction T. An index stating the position in the row, together with the rule for translating locations into the row, then represents the location information.

The frequency at which the ultrasonic pulses are successively emitted and the transport speed of the bank note are so chosen that at least five transmission values are captured in each capture region 60 along the transport direction of the bank note. In the example, transmission values are captured at an interval of 3 mm, preferably 2 mm, along the transport direction, or fifty or more transmission values.

Figure 8:
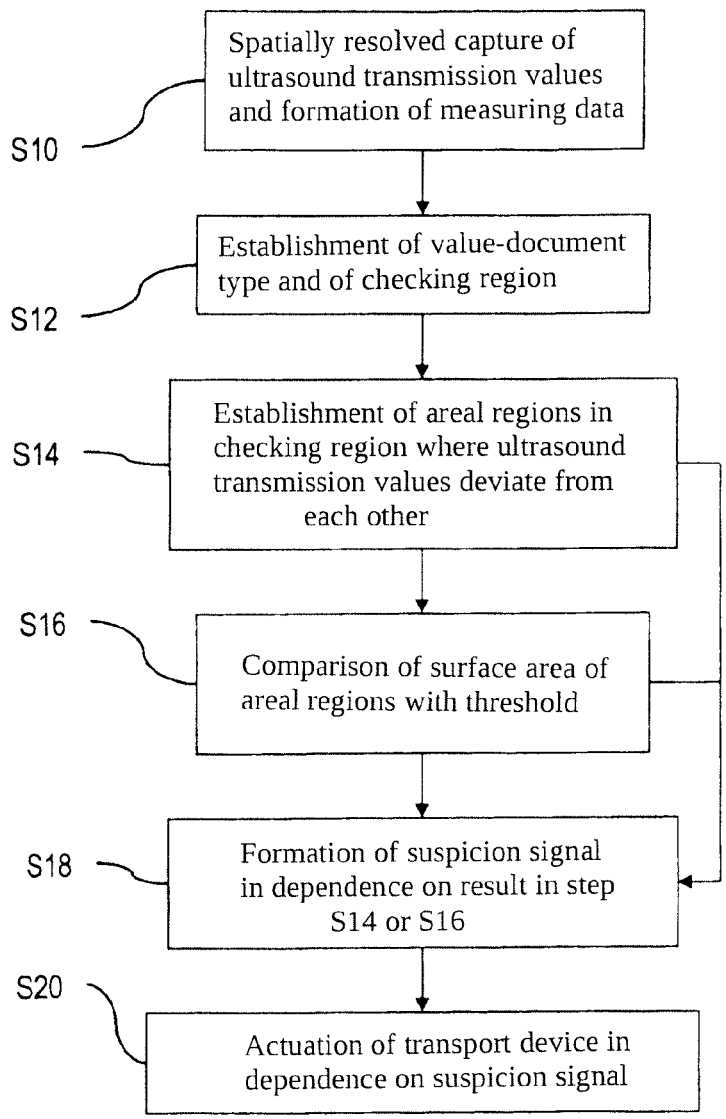
Figure 9:
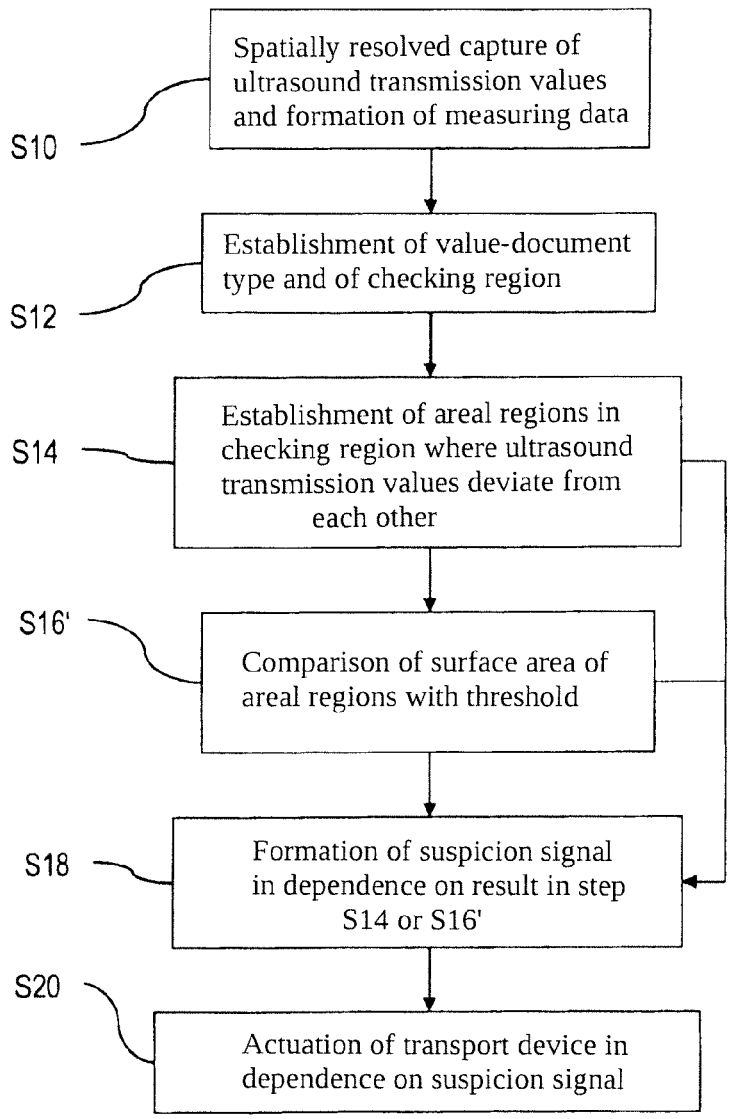

Starting out from these transmission values present for a value document as a function of location, the control and evaluation device 46, more precisely the processor 48, now carries out, when executing program code of the computer program stored in the memory 50, the following method for checking a value document of a specified type for the suspected presence of a forgery, in particular of a pieced-together forgery. The first step S10, however, is carried out partly by the ultrasonic sensor 44. The method is illustrated very schematically as a flowchart in FIG. 8. What is shown is a portion of the method that is run through for each checked value document.

In step S10 the ultrasound transmission is captured as an ultrasonic property of the value document by means of the above-described transmission ultrasonic sensor 44 in a spatially resolved manner so as to form location-dependent measuring data. The measuring data represent the ultrasound transmission in dependence on the location. They are stored temporarily in the memory 50 of the control and evaluation device 46.

Figure 6:
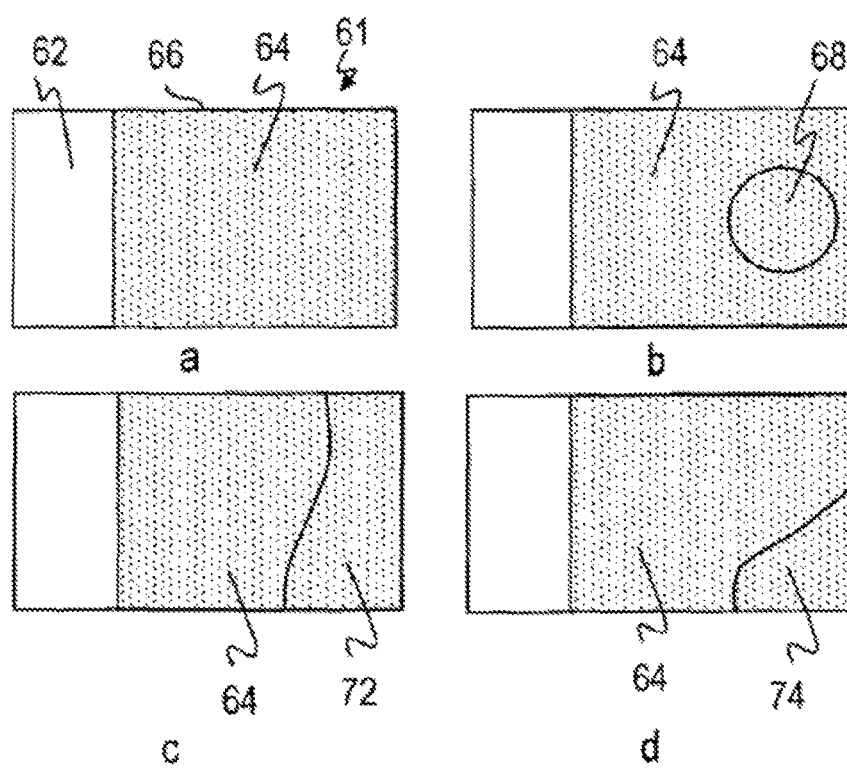

In the example, the control and evaluation device 46 and the method carried out by means thereof or at least partly thereby are designed for checking value documents of two specified value-document types (cf. FIGS. 6a and 7a). Value documents of the two value-document types are distinguishable, on the one hand, by their printed image (not shown in the figures). On the other hand, they have different specified courses of the ultrasound transmission in specified regions.

The first value-document type 61 in FIG. 6a is characterized in that the value documents have a substrate made of bank-note paper which has a region 62 with a watermark and a region 64 with substantially constant ultrasound transmission. The specified first course of the ultrasonic property, i.e. of the ultrasound transmission here, is thus location-independent in the region 64. This region 64 can be employed as a checking region 64, represented by dots in the figures, for the first value-document type. Data for fixing this region relative to the circumferential edge 66 of the value document are stored in the control and evaluation device 46. The latter can also store data from which the ultrasound transmission or an average of measurement values therefor in the checking region 64 are establishable. These data can be established for example by examining reference value documents of the specified type.

FIGS. 6b to d show schematically examples of pieced-together forgeries. In the pieced-together forgery in FIG. 6b, a hole is punched in the region 64 and replaced by paper 68 which has a different weight per unit area from the substrate of the value document in the region 64. In the example, it is about 10 g/m² heavier.

FIGS. 6c and 6d show pieced-together forgeries wherein end portions of the value document lying in the checking region 64 are replaced by sheet regions 72, 74 which have a different weight per unit area from the region 64.

Figure 7:
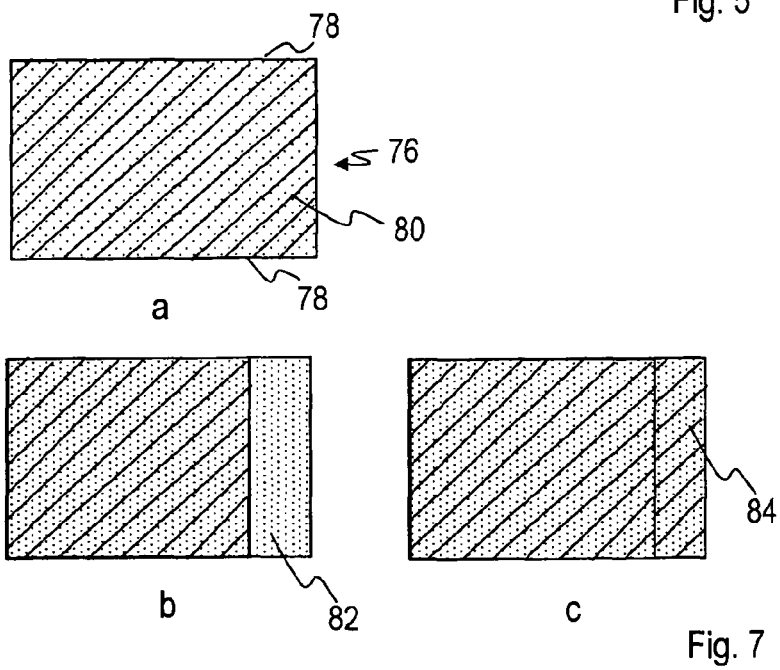

The second value-document type 76 in FIG. 7a has over its total area a bar watermark, marked by hatching in FIG. 7, whose bars, i.e. thicker regions, extend inclined at a specified angle relative to the edges 78 of the value document. The specified course of the ultrasonic property, i.e. of the ultrasound transmission here, corresponds to the course of the thickness over the area of the value document or to a course of the measurement values given by the measuring data, the latter course being captured for the value document by means of the ultrasonic sensor 44. For the second value-document type there can be employed as the checking region 80—again represented by dots—the total value document. Data by means of which the specified course is establishable are stored in the control and evaluation device 46.

FIGS. 7b and 7c represent two examples of pieced-together forgeries. In the example in FIG. 7b, a portion is replaced by a sheet portion 82 without a watermark, in FIG. 7c by a portion 84 with a watermark which, however, is displaced relative to the watermark of the authentic value document.

In the steps S12 to S16, the control and evaluation device 46 checks while employing the location-dependent measuring data whether two areal regions are present in a specified checking region of the value document, so that the at least one ultrasonic property has a specified first course at locations in a first one of the two areal regions, and the at least one ultrasonic property in the first areal region and the at least one ultrasonic property in the other areal region deviate from each other according to a specified difference criterion.

More precisely, the control and evaluation device 46 establishes in step S12, for example in dependence on measuring data which are captured by the remission sensor 40, the type of the value document, here i.e. the currency and denomination of the value document, as well as its position. Methods for this purpose are known to the person skilled in the art. The control and evaluation device then establishes in dependence on the value-document type and according to the established position of the value document the checking region associated with the respective value-document type, in which the locations of the measuring data or ultrasound transmission measurement values used for the further check must lie. In the example, it thus establishes the checking region 64 for a value document of the first value-document type, and the total value document for a value document of the second value-document type.

In the following steps S14 and S16, the control and evaluation device 46 checks while employing the location-dependent measuring data whether two areal regions are present in the value document's checking region specified for the value-document type, so that in a first one of the areal regions the ultrasonic property, i.e. the ultrasound transmission here, has a specified first course at locations in a first one of the two areal regions.

In the case of the first value-document type, the control and evaluation device 46 establishes track-wise portions of the value document in which the ultrasound transmission is constant or location-independent according to a specified criterion. For this purpose, it establishes for different contiguous portions along a track the averages over the measurement values and the amount of the deviations of the measurement values from the average. If the amount of the deviations is smaller than a limiting value specified in dependence on the ultrasonic sensor 44 and the value-document type, the variations of the measurement values are regarded as random fluctuations of the measurement values due to noise and manufacturing-based fluctuations of the value document, and the measurement values are regarded as location-independent. As soon as a measurement value occurs whose deviation is greater, said value is no longer included in a portion of measurement values of the same size. By comparison of the tracks there can thus be obtained the first areal region, which results from directly neighboring portions of neighboring tracks with measurement values rated as equal being fixed as the first areal region.

The remaining portions that are directly neighboring constitute, depending on their position, one or more second areal regions with deviating ultrasonic properties. In the present example, there is employed as a difference criterion with regard to the first value-document type as a subcriterion whether for the second areal region or each of the second areal regions the average over the measurement values for the respective areal region from the average over the measurement values for the first area portion is greater than value which corresponds to a difference in the weights per unit area of value documents of more 5 g/m².

For the second value-document type, the measurement values are tested as to in which regions they have the specified first course given by the watermark, or the pattern given by the watermark. A region in which this is the case constitutes the first areal region. The remaining areal regions that differ from the specified pattern by having no systematic variation or no continuation of the pattern from the first areal region constitute the second areal region or regions.

The distinguishing criterion with regard to the second value-document type comprises the subcriterion of whether no pattern (cf. FIG. 7b) or a different pattern is present in the respective second areal region, or the pattern is displaced (cf. FIG. 7c) and/or rotated relative to the pattern in the first areal region.

If no two areal regions differing according to the subcriterion are found for the respective value-document type, this is understood as an indication that a pieced-together forgery was unable to be recognized. The method is then continued with step S18 wherein a suspicion signal is formed which indicates that no suspicion of forgery is present, and a corresponding datum is stored in the control and evaluation device.

If the check in step S14 yields that two areal regions with the stated properties were found, there is additionally checked in the step S16, which can be omitted in other exemplary embodiments, the further subcriterion of whether the surface areas of the found areal regions exceed a specified minimum surface area of 1 cm², in the example. If this is not the case, the presence of a pieced-together forgery is not assumed, and step S18 as described above is carried out directly thereafter.

A further exemplary embodiment differs from the first exemplary embodiment only in that the step S16 is replaced by a step S16'.

In step S16' a different subcriterion is checked. More precisely, when checking whether the two areal regions are present, only those areal regions are taken into consideration that are limited by at least two portions of the edge that are not collinear. This is effected in the present example by first checking in step S18 whether the two areal regions extend up to portions of the circumferential edge of the value document, as is the case for example in the cases of FIGS. 6b and 6c as well as 7b. Then it is checked whether the portions are not collinear, which is done in the present example by checking whether one of the portions extends in the longitudinal direction and one in the transverse direction of the value document, or whether the portions oppose each other. Only if this is the case, the presence of a pieced-together forgery is assumed and in step S18 a corresponding authenticity signal formed.

In the following step S20 the control and evaluation device 46 so actuates the transport device, in dependence on the authenticity signal and corresponding signals which were established on the basis of the other sensors, that the value document is transported into a corresponding output pocket.

Further exemplary embodiments differ from the above-described exemplary embodiments solely in that, when examining the first value-document type, an averaging of the ultrasound transmission or of the measurement values representing it is effected not over neighboring locations in the same track, but over the nearest neighboring locations of a given location.

Other exemplary embodiments differ from the described exemplary embodiments in that, for establishing the at least one ultrasonic property, ultrasound is emitted onto the value document and the ultrasound remitted by the value document is captured. The described method steps are then performed accordingly.

Another preferred embodiment differs from the first exemplary embodiment in that the ultrasonic transducers are so configured that they are well suited for emitting or receiving ultrasonic pulses with a duration in the range of about 45 μs and an ultrasonic frequency, i.e. a frequency maximum of the spectrum of the ultrasonic pulse, of about 300 kHz. Further, they are so dimensioned that a spot acoustically irradiated upon acoustic irradiation with the ultrasonic pulses on a bank note transported along the transport path 22 has a diameter of about 3 mm.

In other embodiments, the ultrasonic paths can also be inclined relative to the plane of the bank note to be examined, in order to avoid the influence of echoes when employing ultrasonic pulses.

Further, the ultrasound can also be emitted continuously instead of in pulses. In this case, the ultrasonic paths are preferably likewise inclined relative to the bank note to be examined, in order to avoid the occurrence of standing waves.

Furthermore, other exemplary embodiments can differ from those described hereinabove in that the ultrasonic transducers are disposed along a line extending transverse to the transport direction.

The described exemplary embodiments are in particular suitable for checking value documents of a system of value documents which comprises at least two different value-document types which respectively have by a carrier material specific to the respective value-document type, preferably bank-note paper and/or plastic-foil substrates for bank notes and/or composite materials made of paper and foils, having a weight per unit area specific to the respective value-document type, with the weights per unit area differing for at least different value-document types. For example, in a specified currency, a bank note with a value of 10 could have a weight per unit area of 65 g/m$^2$ in the checking region, a bank note with a value of 20 a weight per unit area of 75 g/m$^2$ in the checking region, and a bank note with a value of 50 a weight per unit area of 85 g/m$^2$ in the checking region.

The invention claimed is:

1. A method for checking a value document of a specified type for a suspected presence of a forgery, the method comprising:
transmitting and receiving ultrasonic waves such that at least one ultrasonic property of the value document can be determined;
determining said at least one ultrasonic property of the value document in a spatially resolved manner so as to form location-dependent measuring data;
checking, while employing the location-dependent measuring data, whether two areal regions including a first areal region and a second areal region are present in a specified checking region of the value document, so that the at least one ultrasonic property has a specified first course at locations in the first areal region of the value document, and the at least one ultrasonic property in the first areal region and the at least one ultrasonic property in the second areal region of the value document deviate from each other according to a specified difference criterion; and
forming an authenticity signal which represents the result of the check.

2. The method according to claim 1, wherein the step of determining the at least one ultrasonic property includes emitting ultrasound onto the value document and capturing ultrasound transmitted by the value document.

3. The method according to claim 1, wherein the step of checking whether the two areal regions are present in the specified checking region of the value document includes forming and employing averages over the measuring data over at least three neighboring locations for establishing the course in the first areal region and/or when checking the specified difference criterion.

4. The method according to claim 1, wherein the specified first course is such that in the first areal region according to a specified criterion the at least one ultrasonic property is location-independent, or that the measurement values representing the at least one ultrasonic property in the measuring data are location-independent, and wherein the difference criterion contains the subcriterion of whether a weight per unit area of the first and second areal regions corresponding to the measuring data, or weights per unit area represented by the measuring data, differ by at least 5 g/m$^2$.

5. The method according to claim 1, wherein the specified first course represents a local pattern of the at least one ultrasonic property, said pattern being specified for the type of the value document, and the difference criterion contains the subcriterion of whether the measuring data for the second areal region represent a deviating, or no, local pattern of the at least one ultrasonic property.

6. The method according to claim 1, wherein, when checking whether the two areal regions are present, only those areal regions are taken into consideration whose surface areas exceed a specified minimum surface area.

7. The method according to claim 1, wherein the value document has a circumferential edge, and wherein, when checking whether the two areal regions are present, only those areal regions are taken into consideration that are limited by at least two portions of the edge that do not extend colinearly.

8. The method according to claim 1, which is designed for checking value documents of at least two different specified value-document types, and wherein a value-document type of the value document is established, and the checking region is fixed in dependence on the established value-document type.

9. A device for checking value documents at least of one specified type, the device comprising:
- an ultrasonic sensor that includes a transmitter configured to transmit ultrasonic waves such that at least one ultrasonic property of the value document of value can be determined, and the ultrasonic sensor is configured to determine in a spatially resolved manner said at least one ultrasonic property of the value document transported through a capture region of the ultrasonic sensor so as to form location-dependent measuring data; and
- an evaluation device which is configured to
  - receive the measuring data of the ultrasonic sensor,
  - check while employing the location-dependent measuring data whether two areal regions including a first areal region and a second areal region are present in a specified checking region of the value document, so that the at least one ultrasonic property has a specified first course at locations in the first areal region of the value document, and the at least one ultrasonic property in the first areal region and the at least one ultrasonic property in the second areal region of the value document deviate from each other according to a specified difference criterion, and
  - form an authenticity signal which represents the result of the check.

10. The device according to claim 9, wherein the ultrasonic sensor is configured for emitting ultrasound onto the value document and capturing ultrasound transmitted by the value document.

11. The device according to claim 9, wherein the evaluation device is further configured, when checking whether the two areal regions are present in the specified checking region of the value document, to form and employ averages over the measuring data over at least three neighboring locations to establish the course in the first areal region and/or when checking the distinguishing criterion.

12. The device according to claim 9, wherein the evaluation device is so configured that the specified first course is such that in the first areal region according to a specified criterion the at least one ultrasonic property is location-independent, or that measurement values representing the at least one ultrasonic property in the measuring data are location-independent.

13. The device according to claim 9, wherein the evaluation device is so configured that the difference criterion contains the subcriterion of whether a weight per unit area of the first and second areal the areal regions corresponding to the measuring data differ by at least 5 g/m$^2$.

14. The device according to claim 9, wherein the evaluation device is so configured that the specified first course represents a local pattern of the at least one ultrasonic property, said pattern being specified for the type of the value document, and the difference criterion contains the subcriterion of whether the measuring data for the second areal region represent a deviating, or no, local pattern of the at least one ultrasonic property.

15. The device according to claim 9, wherein the evaluation device is further configured such that, when checking whether the two areal regions are present, only those areal regions are taken into consideration whose surface areas exceed a specified minimum surface area.

16. The device according to claim 9, wherein the evaluation device is so configured that, when checking whether the two areal regions are present, only those areal regions are taken into consideration that are limited by portions of a circumferential edge of the value document that do not extend colinearly.

17. The device according to claim 9, which is adapted for checking value documents of at least two different specified value-document types, and wherein the evaluation device is so configured that the checking region is fixed in dependence on an established value-document type of the value document.

18. An apparatus for processing value documents having
- a feeding device for value documents to be processed;
- an output device for value documents which has at least two output portions for receiving processed value documents;
- a transport device for transporting singled value documents from the feeding device along a transport path to the output device;
- a checking device for checking value documents at least of one specified type, the checking device including
  - an ultrasonic sensor that includes a transmitter configured to transmit ultrasonic waves such that at least one ultrasonic property of the value document of value can be determined, and the ultrasonic sensor is configured to determine in a spatially resolved manner said at least one ultrasonic property of the value document transported through a capture region of the ultrasonic sensor so as to form location-dependent measuring data, and
  - an evaluation device which is configured to
    - receive the measuring data of the ultrasonic sensor,
    - check while employing the location-dependent measuring data whether two areal regions including a first areal region and a second areal region are present in a specified checking region of the value document, so that the at least one ultrasonic property has a specified first course at locations in the first area region of the value document, and the at least one ultrasonic property in the first areal region and the at least one ultrasonic property in the second areal region of the value document deviate from each other according to a specified difference criterion, and
    - form an authenticity signal which represents the result of the check;
- wherein the checking device is arranged such that the transport path extends through a capture region of the checking device; and
- the apparatus for processing value documents further comprising a control device which so actuates the transport device in dependence on an authenticity signal of the checking apparatus for a value document transported by the transport device that the value document is transported into an output portion of two output portions that corresponds to the authenticity signal.

19. The apparatus according to claim 18, wherein the ultrasonic sensor is so disposed that it can determine properties of a value document transported by means of the transport device, said properties being determined by the ultrasonic sensor, and can form measuring data representing them, and an establishing device which establishes a value-document type of the value document in dependence on the measuring data and forms a type signal representing the value-document type, and wherein the evaluation device of the checking device is so configured that upon the check it does not take into consideration measuring data of the ultrasonic sensor in dependence on the type signal of the establishing device for regions outside the value document's checking region specified in dependence on the value-document type of the value document.

\* \* \* \* \*